(12) United States Patent
Kelly (10) Patent No.: US 8,530,215 B2
(45) Date of Patent: Sep. 10, 2013

(54) FRUCTANASE

(75) Inventor: Steven Lewis Kelly, Ceredigion (GB)

(73) Assignee: UWS Ventures Ltd., Swansea (GB)

( * ) Notice: Subject to any disclaimer, the term of this patent is extended or adjusted under 35 U.S.C. 154(b) by 0 days.

(21) Appl. No.: 13/203,573

(22) PCT Filed: Feb. 24, 2010

(86) PCT No.: PCT/EP2010/052354
§ 371 (c)(1),
(2), (4) Date: Nov. 7, 2011

(87) PCT Pub. No.: WO2010/097416
PCT Pub. Date: Sep. 2, 2010

(65) Prior Publication Data
US 2012/0225459 A1  Sep. 6, 2012

Related U.S. Application Data

(60) Provisional application No. 61/155,591, filed on Feb. 26, 2009.

(30) Foreign Application Priority Data

Feb. 26, 2009  (GB) .................................. 0903227.7

(51) Int. Cl.
*C12N 9/26* (2006.01)
(52) U.S. Cl.
USPC .......................................................... 435/201
(58) Field of Classification Search
None
See application file for complete search history.

(56) References Cited

U.S. PATENT DOCUMENTS

2011/0252501 A1* 10/2011 Abad et al. .................... 800/275

FOREIGN PATENT DOCUMENTS

| JP | 2006-129729 | * 5/2006 |
| JP | 2006129729 | 5/2006 |
| WO | 2004015111 | 2/2004 |

OTHER PUBLICATIONS

UnitProtKB Accession No. Q27J21, Apr. 2006, 2 pages.*
Machine translation of JP 2006-129729, obtained from http://dossier1.ipdl.inpit.go.jp/AIPN/odse_top_dn.ipdl?N0000=7400 on Oct. 17, 2012, 27 pages.*
Y. Goh, C. Zhang, A. Benson, V. Schlegel, J. Lee and R. Hutkins, "Identification of a putative operon involved in fructooligosaccharide utilization by *Lactobacillus paracasei*," Applied and Environmental Microbiology, Dec. 2006, pp. 7518-7530, vol. 72.
Y. Goh, J. Lee, and R. Hutkins, "Functional analysis of the fructooligosaccharide utilization operon in *Lactobacillus paracasei* 1195," Applied and Environmental Microbiology, Sep. 2007, pp. 5716-5724, vol. 73.
Martel et al., "Expression, purification and use of the soluble domain of *Lactobacillus paracasei* β-fructosidase to optimise production of bioethanol from grass fructans," Biosource Technology 101 (2010) pp. 4395-4402.
Negro, et al., "Inulin-containing biomass for ethanol production," Applied Biochemistry and Biotechnology, vol. 129-32 (2006), pp. 922-932.

* cited by examiner

*Primary Examiner* — David J Steadman
(74) *Attorney, Agent, or Firm* — 24IP Law Group; Timothy R. DeWitt (57) ABSTRACT

The present invention relates to a novel protein and a method for the manufacture thereof. The novel protein according to the invention is a recombinant protein with fructanase activity. The recombinant protein according to the invention is an engineered protein derived from recombinant DNA encoding for the protein. The recombinant protein may be or may comprise a fragment of a naturally occurring protein, i.e. of a naturally occurring fructanase protein.

8 Claims, 4 Drawing Sheets

Fig. 5

SEQUENCE LISTING

<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Synthesized

<400> SEQUENCE: 1
acgtagctag cgctacaagt gcttcgtcta c                          31

<210> SEQ ID NO 2
<211> LENGTH: 51
<212> TYPE: DNA
<213> ORGANISM: Artificial Sequence
<220> FEATURE:
<223> OTHER INFORMATION: Synthesized

<400> SEQUENCE: 2
cgtaggatcc tcagtggtgg tggtggtggt gttttcagt tagttgacca g     51

<210> SEQ ID NO 3
<211> LENGTH: 712
<212> TYPE: PRT
<213> ORGANISM: Lactobacillus paracasei

<400> SEQUENCE: 3

```
Met Ala Ser Ala Ser Ser Ala Ser Ser Thr Gln Ile Ser Gln Thr Asn
1               5                   10                  15

Thr Gly Ser Gln Pro Asn Asn Glu Thr Thr Gly Glu Thr Ala Gln Ser
            20                  25                  30

Ser Val Asn Ser Thr Ala Thr Ala Ser Ser Ser Val Ala Asp Leu
        35                  40                  45

Pro Ser Ser Ser Asp Ser Lys Ser Ser Ile Gly Ser Thr Ile Ser Gln
    50                  55                  60

Pro Thr Val Asp Lys Lys Glu Thr Ser Lys Ser Asp Thr Ala Asp Asn
65                  70                  75                  80

Asp Leu Thr Lys Ser Val Thr Thr Ser Asp Ser Asp Lys Ala Leu Pro
                85                  90                  95

Thr Ser Lys Thr Thr Leu Pro Thr Ser Asn Glu Gln Val Gln Ser Ser
            100                 105                 110

Val Gly Gln Ser Gln Thr Asp Gln Pro Ala Ser Ser Ala Thr Ile Ala
        115                 120                 125

Thr Asn Ala Val Thr Ser Asp Val Ser Gln Asn Asp Gln Tyr Asn Glu
    130                 135                 140

Pro Tyr Arg Asn Gln Tyr His Tyr Ser Ser Ser Gln Asn Trp Ile Asn
145                 150                 155                 160

Asp Pro Asn Gly Leu Phe Tyr Asp Ser Lys Thr Gly Leu Tyr Asn Leu
                165                 170                 175

Tyr Tyr Gln Tyr Asn Pro Glu Gly Asn Gln Trp Gly Asn Met Ser Trp
            180                 185                 190

Gly His Ala Val Ser Lys Asp Leu Ile Asn Trp Thr Gln Glu Asp Val
        195                 200                 205

Ala Ile Pro Met Leu Gln Asn Gln Gly Trp Glu Asp Phe Thr Tyr Thr
    210                 215                 220

Asn Thr Thr Gly Ser Leu Lys Asp Lys Gly Glu Val Arg Tyr Val Gly
225                 230                 235                 240
```

-continued

```
Val Pro Thr Thr Asn Trp Gly Asp Ala Asp Gly Lys Lys Ala Ile Phe
            245                 250                 255

Ser Gly Ser Ile Val Val Asp Thr Asn Val Ser Gly Leu Gly Lys
        260                 265                 270

Asp Ala Ile Leu Ala Phe Tyr Thr Ala Asp Tyr Gln Ile Ala Thr Arg
            275                 280                 285

Lys Asn Asp Gly Ala Glu Asp Gly Trp Gly Thr Trp Ile Gly Leu Thr
        290                 295                 300

Glu Ile Gln Glu Gln His Leu Ala Tyr Ser Leu Asp Gly Gly Lys Thr
305                 310                 315                 320

Phe Ile Gln Tyr Ser Lys Asp Gly Asn Ala Ala Asn Pro Gln Ala Ile
            325                 330                 335

Ile Pro Thr Ser Met Asn Gln Gly Gly Asp Ala Ala Asn Phe Arg Asp
            340                 345                 350

Pro Ser Val Val Tyr Asp Ala Val Asn Lys Gln Tyr Tyr Leu Thr Val
            355                 360                 365

Val Ser Gly Gln Gln Ala Leu Ile Tyr Lys Ser Ser Asn Leu Leu Asp
        370                 375                 380

Trp Thr Tyr Ala Ser Lys Ile Glu Arg Glu Asn Asp Val Gly Asn Gly
385                 390                 395                 400

Val Trp Glu Cys Pro Ser Leu Val Pro Met Lys Val Ala Gly Thr Asn
            405                 410                 415

Glu Thr Lys Trp Val Phe Cys Ile Ser Val Gln Gln Gly Ala His Ala
            420                 425                 430

Thr Gly Ser Gly Met Gln Tyr Tyr Val Gly Asn Met Thr Ala Asp Gly
        435                 440                 445

Thr Trp Val Pro Glu Ser Ser Lys Thr Leu Gln Asn Pro Met Thr Met
        450                 455                 460

Asp Ser Gly Glu Asp Phe Tyr Ala Gly Ile Pro Phe Ser Asn Met Pro
465                 470                 475                 480

Asp Gly Arg Thr Val Met Leu Ala Trp Gln Ser Asn Trp Ser Tyr Val
            485                 490                 495

Asp Glu Ala Lys Thr Ser Pro Trp Ser Gly Asn Met Thr Leu Pro Arg
            500                 505                 510

Glu Leu Ser Leu Lys Lys Asn Ala Asp Thr Thr Asp Gly Tyr Leu Leu
        515                 520                 525

Thr Asn Thr Val Val Lys Glu Ile Ala Asn Asn Glu Glu Ala Asn Val
        530                 535                 540

Ile Asn Lys Ala Glu Ser Asn Phe Thr Val Ser Arg Ser Asp Glu Gln
545                 550                 555                 560

Val Gln Tyr Glu Gly Lys Gln Tyr Lys Ile Ser Ala Thr Phe Ser Trp
            565                 570                 575

Asp Glu Ala Asp Lys Pro Lys Ser Val Gly Phe Lys Leu Arg Val Ser
            580                 585                 590

Asp Asp Gln Lys Tyr Asp Met Ile Val Gly Tyr Asp Leu Thr Thr Gly
        595                 600                 605

Leu Leu Tyr Val Gln Arg Leu Asn Thr Gly Glu Pro Asn Met Gly Ala
        610                 615                 620

Pro Arg Asp Lys Met Asn Ala Thr Val Asn Ala Asp Gly Ser Ile Thr
625                 630                 635                 640

Ile Thr Val Tyr Val Asp Glu Thr Ser Ile Glu Ala Phe Ala Asn Asp
            645                 650                 655

Gly Glu Lys Ser Ile Thr Gln Asn Phe Phe Met Arg Pro Glu Asn Ile
```

-continued

```
                660                 665                 670
Gly Asp Gln Ala Thr Thr Gly Val Tyr Val Tyr Ser Asn Asp Gly Thr
                    675                 680                 685

Thr Lys Ile Ser Asp Leu Thr Ile Asn Pro Ile Thr Ser Ile Trp Asn
    690                 695                 700

Ser Thr Gly Gln Leu Thr Glu Lys
705                 710

<210> SEQ ID NO 4
<211> LENGTH: 1376
<212> TYPE: PRT
<213> ORGANISM: Lactobacillus paracasei

<400> SEQUENCE: 4

Met Glu Met Asp Glu Lys Lys His Tyr Lys Met Tyr Lys Ser Lys Ser
1               5                   10                  15

Val Trp Val Phe Ala Cys Leu Ser Thr Cys Leu Ile Val Ser Phe Phe
            20                  25                  30

Asn Asp Gly Gln Asn Val Ser Ala Ala Thr Ser Ala Ser Ser Thr Gln
        35                  40                  45

Ile Ser Gln Thr Asn Thr Gly Ser Gln Pro Asn Asn Glu Thr Thr Gly
    50                  55                  60

Glu Thr Ala Gln Ser Ser Val Asn Ser Thr Ala Thr Ala Ser Ser Ser
65                  70                  75                  80

Ser Val Ala Asp Leu Pro Ser Ser Asp Ser Lys Ser Ser Ile Gly
                85                  90                  95

Ser Thr Ile Ser Gln Pro Thr Val Asp Lys Lys Glu Thr Ser Lys Ser
            100                 105                 110

Asp Thr Ala Asp Asn Asp Leu Thr Lys Ser Val Thr Thr Ser Asp Ser
        115                 120                 125

Asp Lys Ala Leu Pro Thr Ser Lys Thr Thr Leu Pro Thr Ser Asn Glu
    130                 135                 140

Gln Val Gln Ser Ser Val Gly Gln Ser Gln Thr Asp Gln Ser Ala Ser
145                 150                 155                 160

Ser Ala Thr Ile Ala Thr Asn Ala Val Thr Ser Asp Val Ser Gln Asn
                165                 170                 175

Asp Gln Tyr Asn Glu Pro Tyr Arg Asn Gln Tyr His Tyr Ser Ser Ser
            180                 185                 190

Gln Asn Trp Ile Asn Asp Pro Asn Gly Leu Phe Tyr Asp Ser Lys Thr
        195                 200                 205

Gly Leu Tyr Asn Leu Tyr Tyr Gln Tyr Asn Pro Glu Gly Asn Gln Trp
    210                 215                 220

Gly Asn Met Ser Trp Gly His Ala Val Ser Lys Asp Leu Ile Asn Trp
225                 230                 235                 240

Thr Gln Glu Asp Val Ala Ile Pro Met Leu Gln Asn Gln Gly Trp Glu
                245                 250                 255

Asp Phe Thr Tyr Thr Asn Thr Thr Gly Ser Leu Lys Asp Lys Gly Glu
            260                 265                 270

Val Arg Tyr Val Gly Val Pro Thr Thr Asn Trp Gly Asp Ala Asp Gly
        275                 280                 285

Lys Lys Ala Ile Phe Ser Gly Ser Ile Val Asp Thr Asn Asn Val
    290                 295                 300

Ser Gly Leu Gly Lys Asp Ala Ile Leu Ala Phe Tyr Thr Ala Asp Tyr
305                 310                 315                 320

Gln Ile Ala Thr Arg Lys Asn Asp Gly Ala Glu Asp Gly Trp Gly Thr
```

```
            325                 330                 335
Trp Ile Gly Leu Thr Glu Ile Gln Glu Gln His Leu Ala Tyr Ser Leu
            340                 345                 350
Asp Gly Gly Lys Thr Phe Ile Gln Tyr Ser Lys Asp Gly Asn Ala Ala
            355                 360                 365
Asn Pro Gln Ala Ile Ile Pro Thr Ser Met Asn Gln Gly Gly Asp Ala
            370                 375                 380
Ala Asn Phe Arg Asp Pro Ser Val Val Tyr Asp Ala Val Asn Lys Gln
385                 390                 395                 400
Tyr Tyr Leu Thr Val Val Ser Gly Gln Gln Ala Leu Ile Tyr Lys Ser
                405                 410                 415
Ser Asn Leu Leu Asp Trp Thr Tyr Ala Ser Lys Ile Glu Arg Glu Asn
            420                 425                 430
Asp Val Gly Asn Gly Val Trp Glu Cys Pro Ser Leu Val Pro Met Lys
            435                 440                 445
Val Ala Gly Thr Asn Glu Thr Lys Trp Val Phe Cys Ile Ser Val Gln
            450                 455                 460
Gln Gly Ala His Ala Thr Gly Ser Gly Met Gln Tyr Tyr Val Gly Asn
465                 470                 475                 480
Met Thr Ala Asp Gly Thr Trp Val Pro Glu Ser Ser Lys Thr Leu Gln
                485                 490                 495
Asn Pro Met Thr Met Asp Ser Gly Glu Asp Phe Tyr Ala Gly Ile Pro
            500                 505                 510
Phe Ser Asn Met Pro Asp Gly Arg Thr Val Met Leu Ala Trp Gln Ser
            515                 520                 525
Asn Trp Ser Tyr Val Asp Glu Ala Lys Thr Ser Pro Trp Ser Gly Asn
            530                 535                 540
Met Thr Leu Pro Arg Glu Leu Ser Leu Lys Lys Asn Ala Asp Thr Thr
545                 550                 555                 560
Asp Gly Tyr Leu Leu Thr Asn Thr Val Val Lys Glu Ile Ala Asn Asn
                565                 570                 575
Glu Glu Ala Asn Val Ile Asn Lys Ala Glu Ser Asn Phe Thr Val Ser
            580                 585                 590
Arg Ser Asp Glu Gln Val Gln Tyr Glu Gly Lys Gln Tyr Lys Ile Ser
            595                 600                 605
Ala Thr Phe Ser Trp Asp Glu Ala Asp Lys Pro Lys Ser Val Gly Phe
            610                 615                 620
Lys Leu Arg Val Ser Asp Asp Gln Lys Tyr Asp Met Ile Val Gly Tyr
625                 630                 635                 640
Asp Leu Thr Thr Gly Leu Leu Tyr Val Gln Arg Leu Asn Thr Gly Glu
                645                 650                 655
Pro Asn Met Gly Ala Pro Arg Asp Lys Met Asn Ala Thr Val Asn Ala
            660                 665                 670
Asp Gly Ser Ile Thr Ile Thr Val Tyr Val Asp Glu Thr Ser Ile Glu
            675                 680                 685
Ala Phe Ala Asn Asp Gly Glu Lys Ser Ile Thr Gln Asn Phe Phe Met
            690                 695                 700
Arg Pro Glu Asn Ile Gly Asp Gln Ala Thr Thr Gly Val Tyr Val Tyr
705                 710                 715                 720
Ser Asn Asp Gly Thr Thr Lys Ile Ser Asp Leu Thr Ile Asn Pro Ile
                725                 730                 735
Thr Ser Ile Trp Asn Ser Thr Gly Gln Leu Thr Glu Lys Phe Val Asp
            740                 745                 750
```

-continued

Glu Asn Gly Asn Thr Ile Ala Ser Asp Lys Ile Gln Thr Gly Arg Val
    755                 760                 765

Gly Gln Ser Tyr Thr Ser Glu Ser Ala Thr Ile Pro Gly Tyr Val Phe
    770                 775                 780

Val Lys Glu Asn Thr Asp His Ile Asn Ser Asn Gln Leu Tyr Thr Thr
785                 790                 795                 800

Gln Asn Gln Thr Ile Thr Tyr Thr Tyr Arg Ala Ser Gln Ala Ser Val
                805                 810                 815

Val Thr Lys Asp Thr Thr Leu Ala Ala Gly Pro Ser Ala Ala Trp Asn
            820                 825                 830

Ala Ala Asp Asn Leu Val Gly Ala Thr Asp Ala Asp Gly Asn Ala Leu
        835                 840                 845

Ala Val Ser Asp Leu Thr Val Asn Gly Ala Val Asp Pro Lys Thr Pro
    850                 855                 860

Gly Thr Tyr Thr Val Thr Tyr Ser Tyr Thr Asp Ala Thr Gly Asn Lys
865                 870                 875                 880

Ile Ser Lys Lys Ala Thr Val Thr Val Ile Ala Ser Lys Ala Asp Ile
                885                 890                 895

Val Thr Lys Asp Thr Thr Met Val Ala Gly Ala Ser Thr Ile Trp Asn
            900                 905                 910

Ala Ala Asp Asn Phe Val Glu Ala Lys Asn Ala Asp Gly Asn Ala Leu
        915                 920                 925

Thr Val Ser Asp Leu Met Ile Asn Gly Thr Val Asp Ser Lys Thr Pro
    930                 935                 940

Gly Thr Tyr Thr Val Thr Tyr Ser Tyr Thr Asp Ala Ala Gly Asn Lys
945                 950                 955                 960

Ile Asn Lys Glu Ala Ile Val Thr Val Ile Ala Ser Lys Ala Asp Ile
                965                 970                 975

Val Thr Lys Asp Thr Thr Met Val Ala Gly Pro Ser Ala Ala Trp Asn
            980                 985                 990

Ala Val Asp Asn Phe Val Glu Ala Thr Gly Ala Asp Gly Asn Ala Leu
        995                 1000                1005

Ala Leu Ser Asp Leu Thr Val Asn Gly Ala Val Asp Pro Lys Thr
    1010                1015                1020

Pro Gly Thr Tyr Thr Val Thr Tyr Ser Tyr Thr Asp Pro Ala Gly
    1025                1030                1035

Asn Lys Ile Ser Lys Glu Ala Thr Val Thr Val Ile Ala Ser Lys
    1040                1045                1050

Ala Asp Ile Val Thr Lys Asp Thr Thr Met Val Ala Gly Pro Ser
    1055                1060                1065

Ala Thr Trp Asn Ala Val Asp Asn Phe Val Glu Ala Thr Gly Ala
    1070                1075                1080

Asp Gly Asn Ala Leu Ala Leu Ser Asp Leu Thr Val Asn Gly Ala
    1085                1090                1095

Val Asp Pro Lys Thr Pro Gly Thr Tyr Thr Val Thr Tyr Ser Tyr
    1100                1105                1110

Thr Asp Val Ala Gly Asn Lys Ile Ser Lys Glu Ala Ile Val Thr
    1115                1120                1125

Val Ile Ala Ser Lys Ala Asp Ile Val Thr Lys Asp Thr Thr Lys
    1130                1135                1140

Val Ala Gly Pro Ser Ala Thr Trp Asn Ala Ala Asp Asn Leu Val
    1145                1150                1155

Ile Ala Thr Asp Ala Lys Gly Asn Ala Leu Ala Leu Ser Asn Leu
    1160                1165                1170

```
Thr Val Thr Gly Ser Val Asp Ser Lys Thr Pro Gly Thr Tyr Thr
    1175            1180            1185

Val Thr Tyr Ser Tyr Thr Asp Ala Ala Gly Asn Lys Ile Ser Lys
    1190            1195            1200

Glu Ala Thr Val Thr Val Ile Ala Ser Lys Ala Asp Ile Val Thr
    1205            1210            1215

Lys Asp Thr Thr Met Val Ala Gly Pro Ser Ala Ala Trp Asn Ala
    1220            1225            1230

Ala Asn Asn Leu Val Ser Ala Thr Asp Ala Asp Gly Asn Ala Leu
    1235            1240            1245

Ala Met Ser Asn Leu Thr Val Thr Gly Thr Val Asp Leu Lys Thr
    1250            1255            1260

Gln Gly Thr Tyr Thr Val Thr Tyr Thr Tyr Thr Asp Val Ala Gly
    1265            1270            1275

Asn Lys Ile Ser Lys Glu Ala Thr Val Thr Val Leu Thr Glu Lys
    1280            1285            1290

Glu Thr Asn Ile Glu Asp Asn Thr Gly Ser Ser Ile Ser Asn Asp
    1295            1300            1305

Arg Glu Asn Pro Pro Ala Ser Ile Thr Gly Lys Gly Gly Asp Asp
    1310            1315            1320

Ile His Gln Asn Ala Lys Thr Thr Met Thr Lys Lys Lys Thr Glu
    1325            1330            1335

Thr Leu Pro Gln Ala Gly Asn His Val Asn Glu Leu Ala Ile Val
    1340            1345            1350

Leu Gly Gln Met Ile Leu Ala Ile Cys Val Gly Gly Ile Leu Trp
    1355            1360            1365

Leu Lys Arg Arg Val Lys Arg Val
    1370            1375
```

FRUCTANASE

CROSS-REFERENCE TO RELATED APPLICATIONS

The present application claims benefit of the filing of U.S. provisional application 61/155,591 filed Feb. 26, 2009 and of UK application GB 0903227.

The sequence listing electronically filed herewith is hereby incorporates by reference in its entirety (File Name: 4091-55004Seq_ListCorrected3.txt; File Size: 18 KB; Date Created May 15, 2012).

FIELD OF THE INVENTION

The present invention relates to recombinant proteins. In particular, the present invention relates to proteins having fructanase activity and a method for their production.

INTRODUCTION

Fructans or fructooligosaccharides (FOS) are sugar polymers containing fructose molecules as well as fructose-glucose disaccharides. Fructans contain a core sucrose group (fructose and glucose) and an extension using fructose. Chemical bonds linking fructose and glucose differ from chemical bonds linking fructose to fructose. Fructans are often found in plants and play an important role in food industry and in probiotics or prebiotics (Prebiotics are carbon source for good bacteria. Humans can not metabolize these prebiotics). Examples of fructans are inulin or levan, both of which are fructose containing linear polysaccharides. Recent development indicates that fructans may also be used for the production of bio fuels, such as but not limited to bio-ethanol.

The production of bio-ethanol as well as many other processes utilising fructan as a carbon source for growth requires the hydrolysis of fructans in order to obtain monosaccharides such as fructose or glucose. The hydrolysis of fructans may be performed by naturally occurring enzymes such as a β-fructosidase precursor (fosE) as suggested in Goh et al., ("Functional Analysis of the Fructooligosaccharide Utilization Operon in *Lactobacillus paracasei* 1195"; Applied and Environmental Microbiology, September 2007, p. 5716-5724). Extracellular enzymes such as inulinase that hydrolyse fructans are extracted from *Aspergillus niger* and are commercially available. These extracellular enzymes are naturally occurring enzymes that are isolated or extracted from their natural environments. However, these fructanase extracellular enzymes are expensive and difficult to obtain in sufficient amounts and good purity for large scale applications.

SUMMARY OF THE INVENTION

The present invention relates to a novel protein and a method for the manufacture thereof. The novel protein according to the invention is a recombinant protein with fructanase activity. The recombinant protein according to the invention is an engineered protein derived from recombinant DNA encoding for the protein. The recombinant protein may be or may comprise a fragment of a naturally occurring protein, i.e. of a naturally occurring fructanase protein. The recombinant protein may be an enzyme. The fragment may have an amino acid sequence corresponding essentially to Seq. ID 3 or a homologue or variant thereof or may be a similar related sequence.

The fructanase activity of the recombinant protein may have advantageous properties for production and hydrolysis of fructans. The recombinant protein may hydrolyse at least one type of fructan to obtain sugar molecules. The fructose may be D-fructose and the glucose in fructan may be D-glucose. The protein may thus be termed fructanase. The protein may also be a levanase, and in this case the protein will hydrolyse levans, or an inulinase where the protein will hydrolyse inulin. Other polysaccharides may also serve as substrates.

Examples of fructans are inulin, levan, 1-kestose, nystose, raffinose, stachyose and melezitose or a combination thereof.

The recombinant protein may be a peptide. The protein may have a molecular weight of less than about 140 kDa. The protein may have a molecular weight of less than about 100 kDa. As a non-limiting an example, the protein may have a molecular weight of about 81.1 kDa.

The recombinant protein may comprise a portion of the amino acid sequence of a β-fructosidase precursor (fosE). The fosE may be fosE of lactic acid bacteri such as *Lactobacillus*, *Leuconostoc*, *Pediococcus*, *Lactococcus*, and *Streptococcus* or the like. For example *Lactobacillus paracasei*, *Lactobacillus casei*, *Lactobacillus rhamnosus* or others may be used. The recombinant protein may also be from another organism e.g. prokaryote or eukaryote.

The portion or fraction may be a domain or a core domain of fosE. The portion may be an amino acid sequence encoding for a certain region of fosE. However, modification may be made to this portion in a usual manner. Further amino acids or an amino acid sequence may be added to the portion or certain amino acids may be removed or replaced in a usual manner well known in the art. For example, the portion may have a modified N-terminal and a modified C-terminal amino acid sequence.

The protein may comprises one or more tags. For example, the tags may be used for purification. One or more hisitidine residues may be added to form one or more polyhistidine tags (his-tags). For example, a his-tag may be added at the C-terminal side of the portion. Other tags known in the art may also be used for the purification of the protein.

An expression vector, such as pET17b or other vectors known in the art may be attached to a DNA sequence encoding the protein to enable production in an appropriate host.

The protein of the invention may be used in the fermentation of fructans and to produce monosaccharides from fructans as, for example, a step in the production of ethanol from fructans. Other uses may be in processing of fructans to release fructose.

The invention also relates to DNA encoding for the recombinant protein. The invention further related to an expression system or expression construct for expressing the recombinant protein. The recombinant protein may be expressed in prokaryotic or eukaryotic cells, for example in *Escherichia. coli* (*E. coli*).

A preferred method for delivering the expression construct into the cell is transformation or transfection, wherein known substances for alleviating transfer of the expression construct through the cell membrane are within the scope of the present invention.

Genetic material comprising nucleic acids, polynucleotides, RNA and DNA, of either natural or synthetic origin, including recombinant RNA and DNA and antisense RNA and DNA; hammerhead RNA, ribozymes, antigene nucleic acids, both single and double stranded RNA and DNA and analogs thereof, either in combination or not with other elements such as, for example, without limitation, cell specific enhancers, and nuclear localization signals, can be introduced into prokaryotic or eukaryotic cells or organisms via transformation or transfection techniques. The present invention uses an "expression construct", "nucleic acid construct" or alternatively a "nucleotide construct" or alternatively a "DNA construct". The term "construct" is used herein to describe a molecule, such as a polynucleotide may optionally be chemically bonded to one or more additional molecular moieties, such as a vector, or parts of a vector. In a specific—but non-limiting—aspect, a nucleotide construct is exemplified by a DNA expression constructs suitable for the transformation of a cardiac host cell. As used herein, the terms "transformation" and "transfection" are intended to refer to a variety of art-recognized techniques for introducing foreign nucleic acid into a host cell/or tissue, including, for example, without limitation, calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

The invention further relates to a method for the manufacture of a recombinant protein with fuctanase activity, the method comprising: expressing a protein with fructanase activity in an expression system; isolating the protein with fructanase activity, wherein the protein is a recombinant protein that comprises a fragment or a partial sequence of a naturally occurring protein. The protein may be a protein as set out above, i.e the naturally occurring protein may be a naturally occurring fructanase protein. The recombinant protein may be an enzyme. The fragment may have an amino acid sequence corresponding essentially to Seq. ID 3 or a homologue or variant thereof or may be a similar related sequence.

Expressing the protein may be performed using prokaryotic cells such as bacteria, (i.e. *Escherichia. coli* (*E. coli*)). Other expression systems known to a person skilled in the art may also be used.

The isolated protein may be purified for example using a histidine-tag (his-tag) or other tags known in the art. The his-tag may be attached at the C-terminal of the protein.

DETAILED DESCRIPTION

The following description of an embodiment of the invention is purely exemplary and the invention is by no means limited to this embodiment. A person skilled in the art will easily adapt the teachings to other biological systems.

The invention is demonstrated by the example of a truncated polypeptide cloned from the β-fructosidase precursor (fosE) from *Lactobacillus paracasei* (*L. paracasei*). It is evident to a person skilled in the art that the invention may be applied to fosE of other *Lactobacillus* species or other lactic acid bacteria as well as to other natural occurring proteins having fructanase activity.

The truncated polypeptide comprises the N-terminal deletion of signal sequences and the C-terminal deletion of cell-binding motif found in the native protein of *L. paracasei*. The truncated polypeptide was expressed successfully in *Escherichia. coli* (*E. coli*) using pET17b as expression vector and forming a ΔfosE-pET17b construct. Polymerase chain reaction using pfx polymerase was utilised to isolate the open-reading from strain 4134. The N-terminal amino acid sequence MAS comprised part of the NheI restriction site and ATG start triplet. A polyhistidine tag (his-tag) to facilitate purification, a stop codon and a BamHI restriction site were encoded in the primer for PCR corresponding to the C-terminal amino acid sequence.

Primers utilized in this work, referred to as Seq. ID 1 and Seq. ID 2:

```
                                              (Seq.ID 1)
5' ACGTAGCTAGCGCTACAAGTGCTTCGTCTAC (Seq.ID 2)
5' CGTAGGATCCTCAGTGGTGGTGGTGGTGGTGTTTTTCAGTTAGTTGA
CCAG
```

The truncated polypeptide comprises a portion of the amino acid sequence of fosE of *L. paracasei*. The amino acid sequence portion may be termed core domain of the β-fructosidase precursor (ΔfosE) having the amino acid sequence in, which is referred to as Seq. ID 3):
MASASSASSTQISQTNTGSQPNNETTGETAQSSVNSTATASSSSVADLPSSSDS KETSKSDTADNDLTKSVTTSDSD-KALPTSKTTLPTSNEQVQSSVGQSQTDQ-PASSATIATNAVTSDVS QNDQYNEPYRNQYHYS-SSQNWINDPNGLFYDSKTGLYNLYYQYNPEGNQWGNMSWGHAVSKDLI NWTQEDVAIPMLQNQGWEDFTYTNT-TGSLKDKGEVRYVGVPTTNWGDADGK-KAIFSGSIVVDTN NVSGLGKDAILAFYTADYQI-ATRKNDGAEDGWGTWIGLTEIQEQHLAYSLDGGKTFIQYSKDGNAA NPQAIIPTSMNQGGDAANFRDPSVVY-DAVNKQYYLTVVSGQQALIYKSSNLLD-WTYASKIERENDV GNGVWECPSLVPMKVAGTNETK-WVFCISVQQGAHATGSGMQYYVGNMTADGTWVPESSKTLQN PMTMDSGEDFYAGIPFSNMPDGRTVM-LAWQSNWSYVDEAKTSPWSGNMTL-PRELSLKKNADTTD GYLLTNTVVKEIANNEEANVIN-KAESNFTVSRSDEQVQYEGKQYKISATFSWDEADKPKSVGFKLR VSDDQKYDMIVGYDLTTGLLYVQRLNT-GEPNMGAPRDKMNATVNADGSITITVYV-DETSIEAFAN DGEKSITQNFFMRPENIGDQAT-TGVYVYSNDGTTKISDLTINPITSIWNSTGQLTEK An N-terminal amino acid sequence MAS has been added.

This is compared to the amino acid sequence of fosE of *L. paracasei*, referred to as Seq. ID 4:

```
>Q27J21|Q27J21_LACPA Beta-fructosidase -
Lactobacillus paracasei.
MEMDEKKHYKMYKSKSVWVFACLSTCLIVSFFNDGQNVSAATSASSTQISQTNTGSQPNN
ETTGETAQSSVNSTATASSSSVADLPSSSDSKSSIGSTISQPTVDKKETSKSDTADNDLT
KSVTTSDSDKALPTSKTTLPTSNEQVQSSVGQSQTDQSASSATIATNAVTSDVSQNDQYN
EPYRNQYHYSSSQNWINDPNGLFYDSKTGLYNLYYQYNPEGNQWGNMSWGHAVSKDLINW
TQEDVAIPMLQNQGWEDFTYTNTTGSLKDKGEVRYVGVPTTNWGDADGKKAIFSGSIVVD
TNNVSGLGKDAILAFYTADYQIATRKNDGAEDGWGTWIGLTEIQEQHLAYSLDGGKTFIQ
YSKDGNAANPQAIIPTSMNQGGDAANFRDPSVVYDAVNKQYYLTVVSGQQALIYKSSNLL
DWTYASKIERENDVGNGVWECPSLVPMKVAGTNETKWVFCISVQQGAHATGSGMQYYVGN
MTADGTWVPESSKTLQNPMTMDSGEDFYAGIPFSNMPDGRTVMLAWQSNWSYVDEAKTSP
WSGNMTLPRELSLKKNADTTDGYLLTNTVVKEIANNEEANVINKAESNFTVSRSDEQVQY
EGKQYKISATFSWDEADKPKSVGFKLRVSDDQKYDMIVGYDLTTGLLYVQRLNTGEPNMG
APRDKMNATVNADGSITITVYVDETSIEAFANDGEKSITQNFFMRPENIGDQATTGVYVY
SNDGTTKISDLTINPITSIWNSTGQLTEKFVDENGNTIASDKIQTGRVGQSYTSESATIP
GYVFVKENTDHINSNQLYTTQNQTITYTYRASQASVVTKDTTLAAGPSAAWNAADNLVGA
TDADGNALAVSDLTVNGAVDPKTPGTYTVTYSYTDATGNKISKKATVTVIASKADIVTKD
TTMVAGASTIWNAADNFVEAKNADGNALTVSDLMINGTVDSKTPGTYTVTYSYTDAAGNK
INKEAIVTVIASKADIVTKDTTMVAGPSAAWNAVDNFVEATGADGNALALSDLTVNGAVD
PKTPGTYTVTYSYTDPAGNKISKEATVTVIASKADIVTKDTTMVAGPSATWNAVDNFVEA
TGADGNALALSDLTVNGAVDPKTPGTYTVTYSYTDVAGNKISKEAIVTVIASKADIVTKD
TTKVAGPSATWNAADNLVIATDAKGNALALSNLTVTGSVDSKTPGTYTVTYSYTDAAGNK
ISKEATVTVIASKADIVTKDTTMVAGPSAAWNAANNLVSATDADGNALAMSNLTVTGTVD
LKTQGTYTVTYTYTDVAGNKISKEATVTVLTEKETNIEDNTGSSISNDRENPPASITGKG
GDDIHQNAKTTMTKKKTETLPQAGNHVNELAIVLGQMILAICVGGILWLKRRVKRV
```

Figure 1:
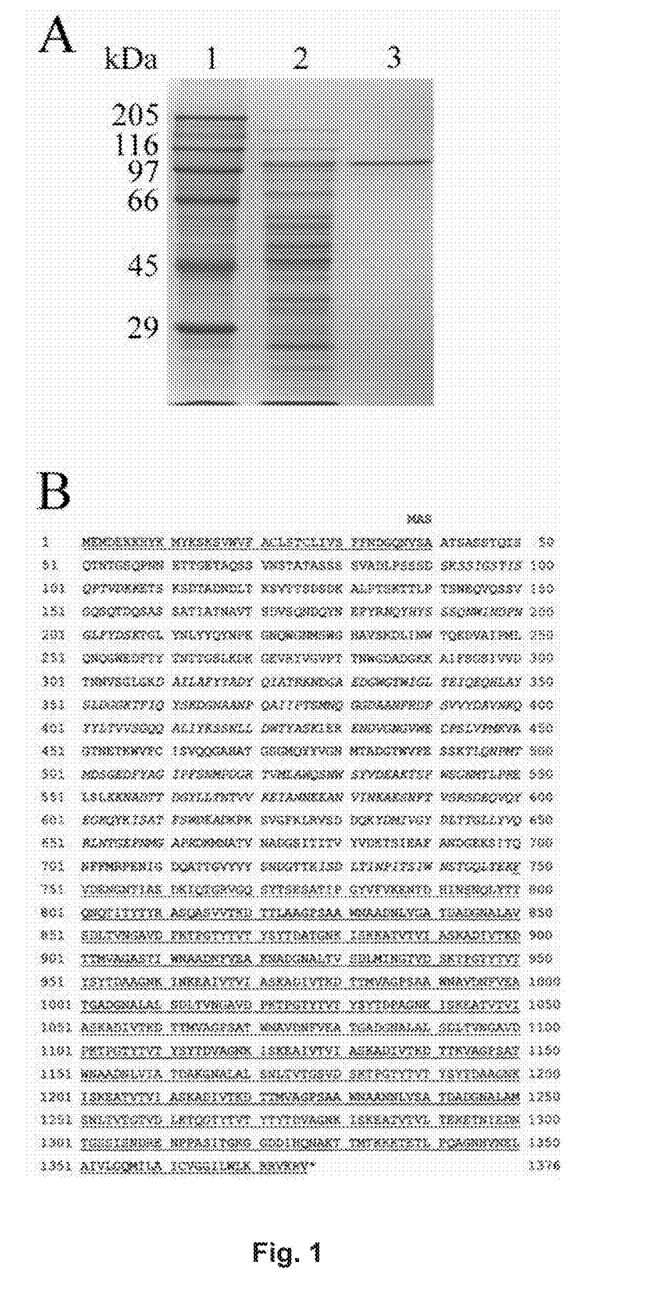
FIG. 1A shows a SDS-PAGE of purified recombinant truncated β-fructosidase precursor (ΔfosE).
FIG. 1B shows an indication of the partial polypeptide sequence of ΔfosE expressed in *E. coli* compared to the native β-fructosidase precursor (fosE) protein's amino acid sequence (not underlined portion).

A direct comparison of ΔfosE sequence and fosE sequence is shown in FIG. 1B. The complete sequence corresponds to the sequence of fosE while the sequences left away for ΔfosE are underlined. Consequently, the non-underlined portion corresponds to the ΔfosE protein sequence.

The ΔfosE sequence is expressed in bacterial system and the recombinant ΔfosE protein is isolated and eventually purified as described below. The obtained ΔfosE protein is en enzyme having fructanase activity, i.e. the ΔfosE protein is a levanase or an inulinase or both, hydrolysing levan and inulin and other fructans.

Heterologous Expression in E. Coli and Isolation of Recombinant ΔfosE protein.

The ΔfosE-pET17b construct was transformed into E. coli strain BL21 (DE3) and positive transformants selected using ampicillin. Overnight cultures (10 ml) of transformants were used to inoculate one litre volumes of Terrific Broth supplemented with 20 g·l$^{-1}$ peptone and 0.1 mg·ml$^{-1}$ sodium ampicillin. Cultures were grown at 37° C., 230 rpm for 7 hours prior to induction with 1 mM IPTG and expression at 30° C., 190 rpm for 18 hours. Recombinant ΔfosE protein was isolated according to the method of Arase et al (Arase M, Waterman M R, Kagawa N; Biochem Biophys Res Commun 2006 May 26; 344(1):400-5. Epub 2006 Mar. 20) except that 2% (w/v) sodium cholate and no Tween20 were used in the sonication buffer. The solubilized ΔfosE protein was purified by affinity chromatography using Ni$^{2+}$-NTA agarose with the modification that 0.1% (w/v) L-histidine in 50 mM sodium phosphate, pH 7.5, 25% (w/v) glycerol was used to elute non-specifically bound E. coli proteins after the salt washes and elution of P450 protein was achieved with 1% (w/v) L-histidine in 50 mM sodium phosphate, pH 7.5, 25% (w/v) glycerol. Isolated ΔfosE protein fractions were stored at −80° C. Protein purity was assessed by SDS polyacrylamide gel electrophoresis and the identity of the purified protein confirmed by trypsin digestion followed by nano-LC/MS/MS of the tryptic peptides released. A SDS page of purified recombinant ΔfosE is illustrated in FIG. 1A.

Determination of Fructanase Activity.

Fructanase activity, in this example exo-fructanase activity, was determined using a discontinuous assay system with the levels of fructose produced being determined at fixed time intervals. The standard assay system consisted of a 1 ml reaction volume of saccharide solution in 0.1 M sodium acetate, pH 5, containing 1.62 ng/ml Ni-NTA agarose purified ΔfosE. Incubation was for 30 minutes at 37° C. prior to the withdrawal of 100 µl for colour development with 0.9 ml of 1 mg/ml 2,3,5-triphenyl tetrazolium chloride in 1 M NaOH (15 minutes at 37° C.). The pink-red colour produced was monitored by the absorbance at 520 nm. The colorimetric assay was standardised against 100 µl of fructose solutions (0 to 6 mM) in 0.1 M sodium acetate, pH 5. Each assay was performed in triplicate. The colorimetric reaction with 2,3,5-triphenyl tetrazolium chloride was found to be 20-fold more sensitive for D-fructose than D-glucose using the conditions described above. Exo-fructanase activity was expressed as nmoles of fructose produced per minute per μg ΔfosE protein.

Protein concentrations were determined by the Coomassie Blue 8250 dye-binding method (BioRad, Hemel Hempstead, UK) using bovine serum albumin standards. Spectral determinations were made using a Hitachi U-3310 UV/VIS spectrophotometer (San Jose, Calif.).

Thermostability Determinations.

Stock solutions (162 μg/ml) of Ni-NTA agarose purified ΔfosE protein were incubated for ten minutes at temperatures ranging from 22 to 90° C. These enzyme solutions were then incubated on ice prior to the commencement of the exo-fructanase assay described above in 10% (w/v) chicory inulin, 0.1 M sodium acetate, pH 5. The inulin was solubilised by warming to 70° C. for 5 minutes followed by cooling to room temperature prior to use.

pH-Profile Determinations.

The pH-profile of ΔfosE protein was determined between pH 3 and 11 using 10% (w/v) chicory inulin dissolved in 0.1 M buffer as described previously. The buffers used were 0.1 M sodium acetate (pHs 3, 3.5, 4, 4.5, 5, 5.5, 6), 0.1 M sodium phosphate (pHs 6.5, 7, 7.5), 0.1 M Tris-HCl (pHs 8, 8.5) and sodium bicarbonate/carbonate (pHs 9, 9.5, 10, 10.5, 11).

Substrate Saturation Determinations.

Substrate specificity for ΔfosE protein was determined using chicory inulin (0.125 to 20% w/v), sucrose (0.025 to 2 M), 1-kestose (0.005 to 0.4 M), nystose (0.0045 to 0.35 M), rafinose (0.02 to 0.48 M), levan (from *Zymomonas mobilis* 0.088 to 3.5% w/v), stachyose (0.04 to 0.4 M) and melezitose (0.04 to 0.4 M) in 0.1 M sodium acetate, pH 5 using the exo-fructanase assay system described previously.

Chemicals.

All chemicals, unless otherwise stated, were obtained from Sigma Chemical Company (Poole, UK). DIFCO growth media were obtained from Becton Dickinson Ltd (Cowley, UK).

Experimental Results

Heterologous Expression and Purification of Recombinant ΔfosE Protein.

Expression of truncated fosE levanase (recombinant ΔfosE protein) in *E. coli* followed by purification using affinity chromatography on Ni-NTA agarose yielded 22.5 nmoles fosE levanase from 1 litre of cell culture which was over 95% pure as resolved by SDS-PAGE (lane 3—FIG. 1A). However, only 35% of the total exo-fructanase activity (as determined using 10% w/v chicory inulin) detected in the cytosolic fraction was recovered, albeit with a 5-fold increased in specific activity. Less than 1% of the exo-fructanase activity was found not to bind to the Ni-NTA agarose matrix. SDS-PAGE (FIG. 1A) indicated that the recombinant ΔfosE protein had an apparent molecular weight of 100 kDa, some 20 kDa greater than that predicted from the amino acid sequence of the truncated fosE enzyme. The identity of the purified ΔfosE protein was confirmed by trypsin digestion of the 100 kDa SDS-PAGE band (FIG. 1A—lane 3) followed by nano-LC/MS/MS, identifying 21 peptides present in ΔfosE protein (Q27J21—full length sequence) which accounted for 50.7% coverage of the truncated protein (FIG. 1B) with a MASCOT score of 3609. Gel exclusion chromatography of ΔfosE protein on Sephacryl S-400HR indicated that the native molecular weight of the ΔfosE protein was 85 kDa (data not shown) when compared against several protein standards ranging in molecular weight from 12 to 700 kDa. While the polypeptide used in the invention had a predicted molecular weight of 81.1 kDa the predicted molecular weight of the native protein is 147 kDa.

Biochemical Characterisation of ΔfosE Protein.

Figure 2:
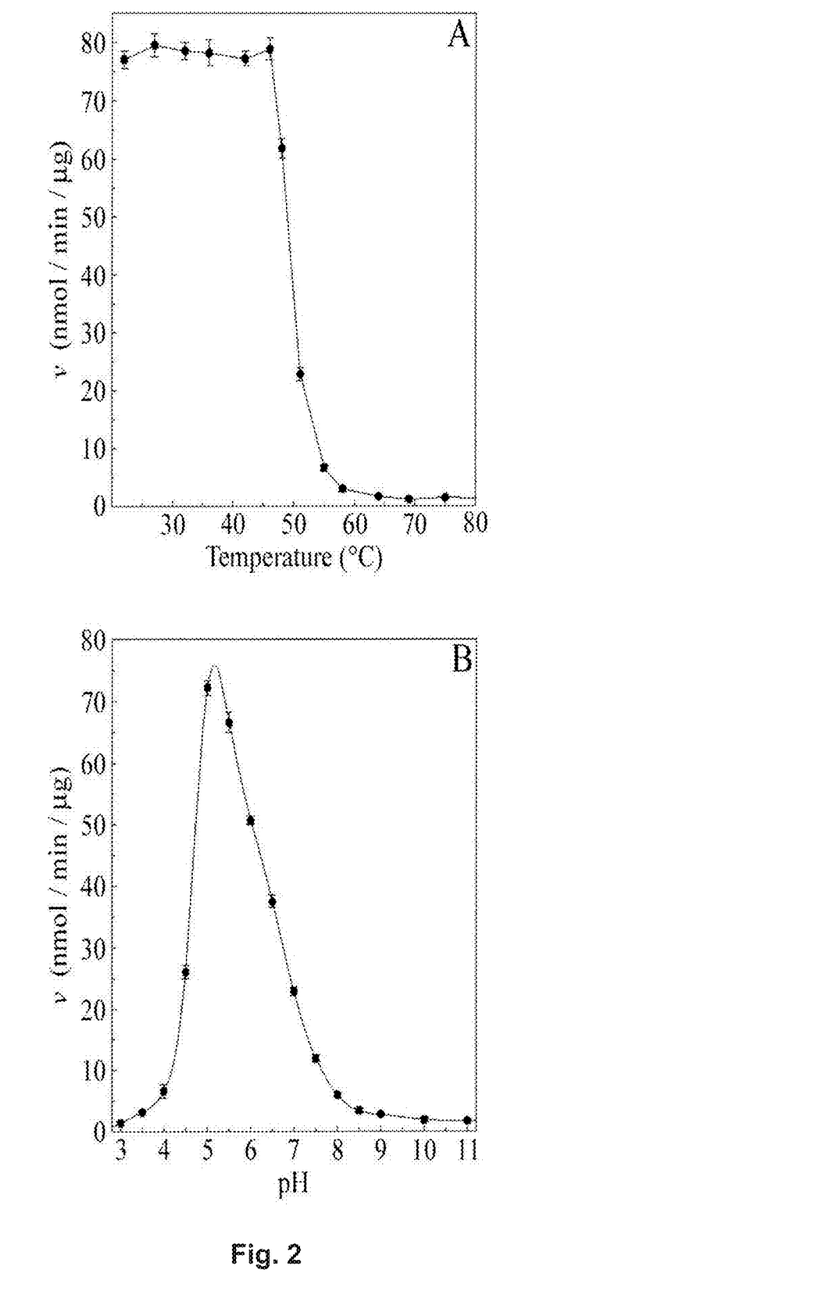
FIG. 2 shows temperature (A) and pH (B) profiles for activity of the recombinant ΔfosE activity using chicory inulin as a substrate.

Thermostability studies (FIG. 2A) indicate that the recombinant ΔfosE protein was stable up to 46° C. for 10 minutes. At temperatures higher than this, the fructanase activity is rapidly lost, with the ΔfosE protein effectively deactivated by temperatures higher than 55° C. The $T_{0.5}$ value for the ΔfosE protein was calculated to be 49° C. under the stated conditions. The pH profile (FIG. 2B) of the ΔfosE protein, using 10% (w/v) chicory inulin, indicated an optimal pH of 5 to 5.5 for the exo-fructanase activity measured, with the activity of the ΔfosE protein falling sharply as the pH fell below 5.0. The decrease in the observed exo-fructanase activity as the pH is increased above 5.0 is gradual, with the ΔfosE protein effectively becoming inactive at pH values above 8.

Figure 3:
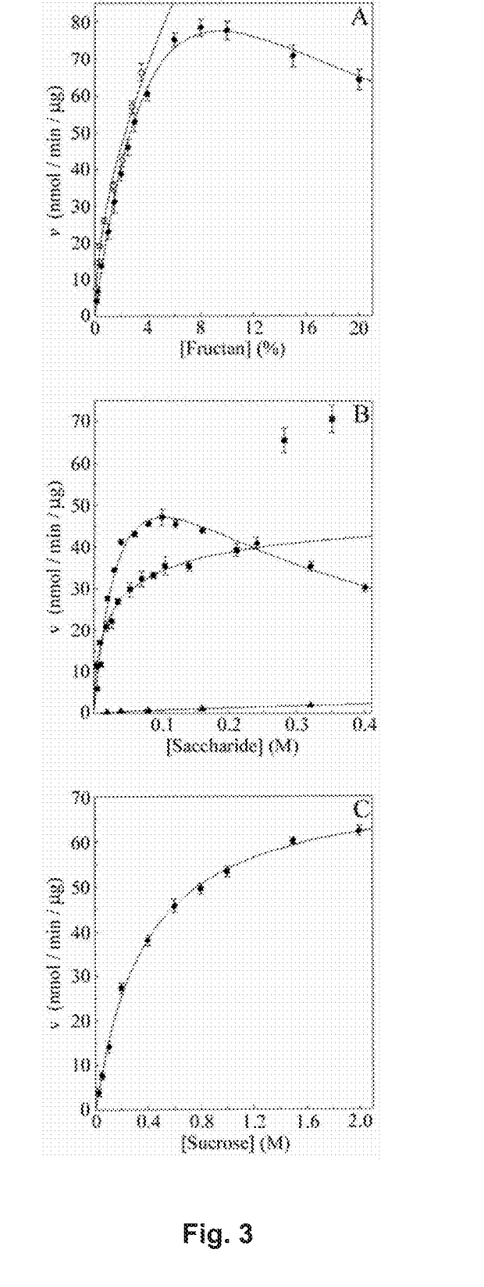
FIG. 3 shows activity profiles using different carbon sources and activity of a recombinant ΔfosE protein.

Substrate saturation experiments with the polyfructans chicory inulin and especially bacterial levan (FIG. 3A) were hampered by the relative insolubility of these compounds in 0.1 M sodium acetate buffer, pH 5. This relative insolubility was partially solved by warming the solutions for 5 minutes at 70° C., which increased the solubility of these the compounds, even when cooled back to room temperature. However, incubation for periods longer than 5 minutes at 70° C. were avoided at this caused the release of free fructose from the polyfructans (probably by acidic hydrolysis of the glycosidic bonds). The bacterial levan became extremely viscous at concentrations 3.5% (w/v) preventing higher concentrations from being used. The chicory inulin solutions above 6% (w/v) became progressively more viscous with the chicory inulin solution progressively changing in appearance from a colourless solution to a viscous white slurry at 25% (w/v). A saturating concentration of bacterial levan could not be obtained due to solubility problems of the bacterial levan, with 3.5% (w/v) levan yielding an exo-fructanase specific velocity of 66 nmol/min/μg. A saturating concentration of 8% (w/v) chicory inulin (78 nmol/min/μg) was obtained above which, the observed enzyme velocity fell with further increase in the chicory inulin concentration. This is indicative of substrate inhibition and $k_m$ and $k_i$ values for chicory inulin of 7.8% and 11.2%, respectively, were calculated by non-linear regression of the Michaelis-Menten single substrate inhibition equation $[v=(V_{max} \cdot [S])/(k_m+([S]^2/k_i)+[S])]$. The inhibition caused by chicory inulin concentrations above 8% (w/v) is likely to be due in part to viscosity effects rather than 'classical' substrate inhibition alone.

Substrate saturation experiments with the oligosaccharides (FIG. 3B) 1-kestose, nystose, rafinose, stachyose and melezitose were less problematic, with no solubility problems encountered up to 0.5 M. The stachyose and the melezitose could not be hydrolysed to produce free fructose by the ΔfosE protein under the stated exo-fructanase assay conditions at concentrations up to 0.5 M saccharide. The rafinose was a relatively poor substrate with a specific velocity of just 2 nmol/min/μg observed in 0.32 M rafinose. This was is in contrast to both the 1-kestose and the nystose. The nystose gave a 'biphasic' substrate saturation curve with the first Michaelis-Menten phase extending up to 0.2 M, yielding a specific velocity of 39 nmol/min/μg and a $k_m$ value of 15.5 mM. At higher nystose concentrations, the velocity significantly increases well beyond what is predicted by either the Michaelis-Menten or Hill equations. The substrate saturation curve obtained with the 1-kestose achieved a maximum velocity of 47 nmol/min/μg at 0.1 M kestose, with further increases in kestose concentration causing a progressive reduction in the observed exo-fructanase velocity. This velocity curve is indicative of substrate inhibition and can be described using the Michaelis-Menten single substrate inhibition equation (see above) with $k_m$ and $k_i$ values of 50 mM and 210 mM, respectively, being obtained for 1-kestose.

The substrate saturation velocity curve obtained with sucrose (FIG. 3C) obeyed Michaelis-Menten kinetics yielding a $k_m$ value of 398 mM and an observed specific velocity of 62 nmol/min/μg with 2 M sucrose. The ability to hydrolyse sucrose into free fructose and glucose is indicative of an invertase/sucrase enzyme. Therefore, the ΔfosE protein exhibits wide-ranging substrate specificity for the exo-fructanase reaction, suggesting that this ΔfosE protein could be a levan(o)sucrase rather than a typical exo-fructanase/levanase/inulinase.

Table 1 shows further characterisation of the ΔfosE protein for the release of fructose from the fructan in grass juice with potential for the optimised production of bioethanol from grass. The table 1 shows efficient release of fructose in column 2 that is abolished on addition of heat denatured protein in column 3 The ΔfosE protein compares well with commercial endo- and exo-inulinase and a combination of these. The release of sugars fermentable by *Saccharomyces cerevisiae* as opposed to the fructan polymer could provide a route to optimal bioethanol production using the novel ΔfosE protein or derivatives thereof made by genetic improvements.

| | Carbohydrate content of growth and fermentation media ($t_0$ hr) | | | | | |
|---|---|---|---|---|---|---|
| | Media | | | | | |
| | 1 GJ | 2 GJ + FosE | 3 GJ + $_{hd}$FosE | 4 GJ + Exo-I | 5 GJ + Endo-I | 6 GJ + Exo/Endo-I |
| Glc (mg mL$^{-1}$) | 7.9 | 8.3 | 8.0 | 8.0 | 8.5 | 8.8 |
| Fru (mg mL$^{-1}$) | 21.5 | 36.8 | 20.6 | 30.5 | 21.3 | 27.8 |
| Fru:Glc | 2.7 | 4.4 | 2.6 | 3.8 | 2.5 | 3.2 |
| ΔGlc (mg mL$^{-1}$) | n.d | +0.5 | +0.2 | +0.2 | +0.6 | +0.9 |
| ΔFru (mg mL$^{-1}$) | n.d | +15.3 | n.d | +9.0 | n.d | +6.3 |
| ΔFru:ΔGlc | n.d | 33.1 | n.d | 50.6 | n.d | 6.8 | n.d = not determined
Δ = change (±) in glc or fru content following enzyme addition
Glucose concentrations quantified using a Glucose Assay Kit (GAGO-20, SIGMA).
Fructose concentrations quantified using a colorimetric assay for six-carbon ketohexoses (not glucose).

Figure 4:
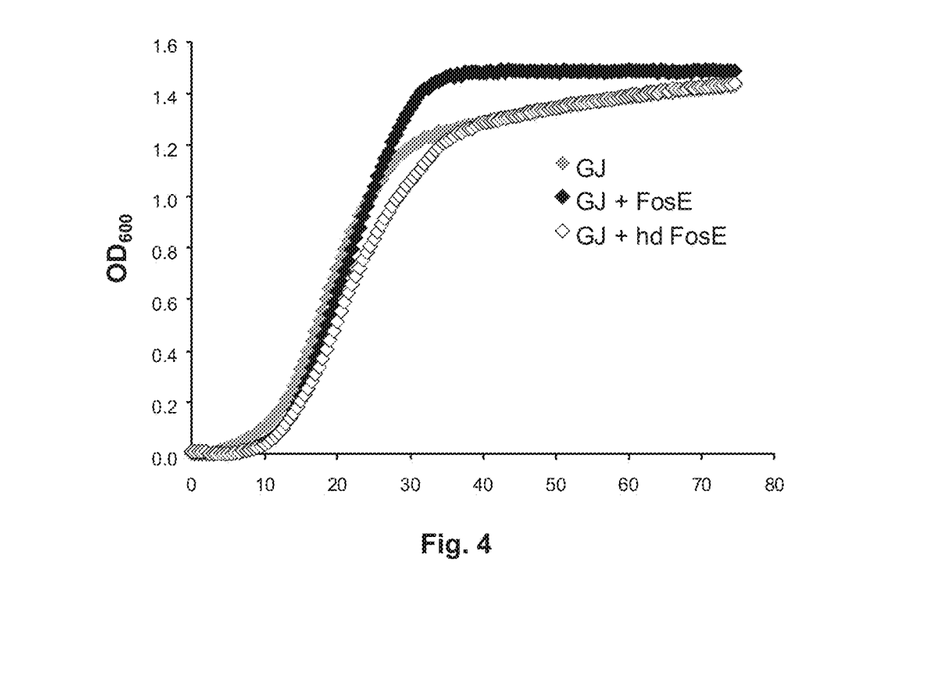
FIG. 4 illustrates the growth of yeast on grass juice and in the presence of recombinant ΔfosE and when heat denatured.

This is supported by the examination of growth characteristics in FIG. 4 which illustrates the growth of yeast on grass juice and in the presence of recombinant ΔfosE protein and when heat denatured. The presence of the active protein allows enhanced growth compared to a heat denatured form.

Figure 5:
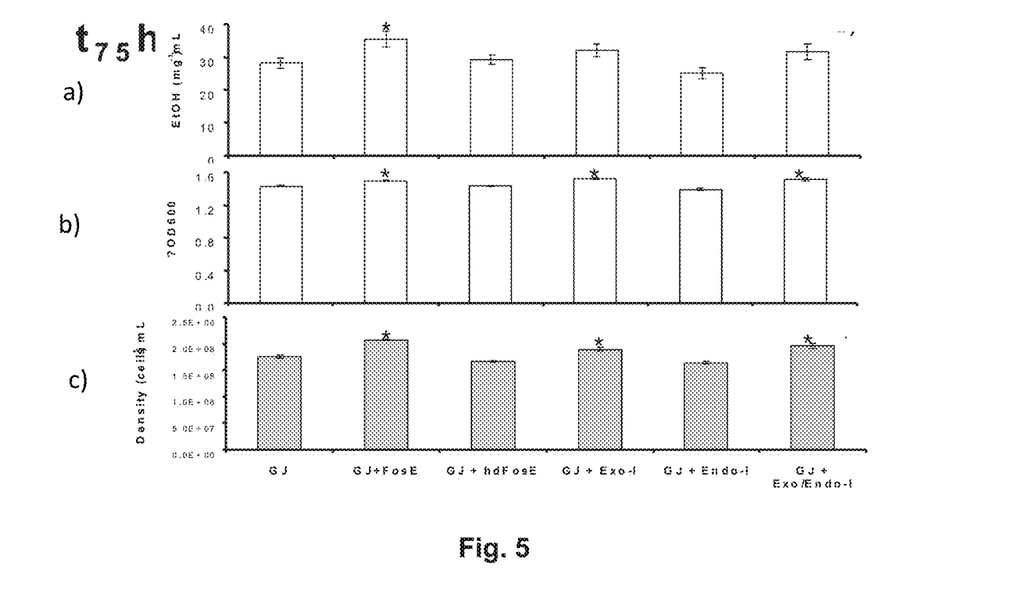
FIG. 5. shows measurements of a) ethanol yield, b) optical density and c) cell numbers estimated by haemocytometer counts for *Saccharomyces cerevisiae* grown on untreated grass juice (GJ), GJ+recombinant ΔfosE, GJ+$_{hd}$ recombinant ΔfosE, GJ+Exo-Inulinase, GJ+Endo-Inulinase and GJ+Exo/Endo-Inulinase ($t_{75}$ hr). *=significantly higher (Student's t-test, P<0.05, n=3) values than those seen on untreated GJ.

FIG. 5 shows measurements of a) ethanol yield, b) optical density and c) cell numbers estimated by haemocytometer counts for *Saccharomyces cerevisiae* grown on untreated grass juice (GJ), GJ+recombinant ΔfosE, GJ+$_{hd}$ recombinant ΔfosE, GJ+Exo-Inulinase, GJ+Endo-Inulinase and GJ+Exo/Endo-Inulinase ($t_{75}$ hr). *=significantly higher (Student's t-test, P<0.05, n=3) values than those seen on untreated GJ.

The invention claimed is:

1. An isolated protein with fructanase activity, wherein the protein comprises the amino acid sequence of SEQ ID NO:3.

2. The isolated protein according to claim 1, wherein the protein is isolated from *Lactobacillus paracasei*.

3. The isolated protein according to claim 1, wherein the protein further comprises at least one histidine residue.

4. The isolated protein according to claim 1, wherein the protein comprises a tag.

5. The isolated protein according to claim 1, wherein the fructanase activity comprises the ability to hydrolyse a fructan.

6. The isolated protein according to claim 5, wherein the fructan is at least one of inulin, levan, 1-kestose, nystose, rafinose, stachyose and melezitose or a combination thereof.

7. The isolated protein according to claim 1, wherein the protein is soluble in an aqueous solution.

8. The isolated protein according to claim 1, recombinantly expressed in a prokaryotic or an eukaryotic cell.

* * * * *